United States Patent [19]

Perkins et al.

[11] Patent Number: 5,724,379

[45] Date of Patent: Mar. 3, 1998

[54] METHOD OF MODIFYING COMPARABLE HEALTH CARE SERVICES

[75] Inventors: Nancy A. K. Perkins, Canandaigua; Nancy N. Boyer, Penfield; Catherine H. Dibble, Honeoye Falls; Catherine G. McCabe, Rochester, all of N.Y.

[73] Assignee: HealthChex, Inc., Fairport, N.Y.

[21] Appl. No.: 361,167

[22] Filed: Dec. 21, 1994

Related U.S. Application Data

[63] Continuation of Ser. No. 38,351, Mar. 29, 1993, abandoned, which is a continuation of Ser. No. 517,257, May 1, 1990, abandoned.

[51] Int. Cl.$^6$ .............................. G06F 17/60; G06G 7/52
[52] U.S. Cl. .......................... 395/202; 395/203; 395/207; 395/211
[58] Field of Search ................................ 395/201, 202, 395/203, 204, 207, 211; 364/400, 401, 406, 408, 413.01, 413.02

[56] References Cited

U.S. PATENT DOCUMENTS 5,018,067  5/1991  Mohlenbrock et al. ................ 128/630

OTHER PUBLICATIONS

*Hospitals*, vol. 61, p. 74, May 5, 1987, Powills, "Employees look to Ryder for MD referrals".

*Wall Street Journal*, 3 Star Eastern, Aug. 4, 1987, p. 37, "New Corporate Program Lets Employees Compare Local Doctors' Fees and Training".

*Fort Lauderdale News*, Nov. 15,1987, p. D1, "Physicians' rating cuts Ryder costs".

Data Pro, 1996 McGraw–Hill Inc., Delran, NJ, p. 045–200–003.

*Modern Healthcare*, vol. 15, No. 19, p. 110 (abstract only), Sep. 13, 1985, Mazzoni "Hospital Group, Software Firm Join to Market Data, Consulting".

*Abst. Hosp. Mgmt. Stud.*, 1974, 11/1, Liaropoulos, "A measure of productive efficiency with application in incentive reimbursement for hospital care".

*Modern Healthcare*, vol. 16, No. 13, p. 52 (abstract only), Jun. 20, 1986, Carter "PCs Can Tap Databanks for Costs".

*National Underwriter*, vol. 91, No. 13, pp. 25, 37 (abstract only), Mar. 30, 1987, Maxie "A Look at Six Health–Care Info Systems".

*Arch. Intern. Med.*, 149, No. 5, 1989, pp. 1185–1188 (abstract only), Stern et al., "A comparison of length of stay and costs for health maintenance organization and fee–for–service patients".

Horn; "Measuring Severity of Illness: Comparisons Across Institutions"; *American Journal of Public Health*; v73 n1; Jan. 1983; pp. 25–31.

(List continued on next page.)

*Primary Examiner*—Gail O. Hayes
*Assistant Examiner*—Stephen R. Tkacs
*Attorney, Agent, or Firm*—Eugene Stephens & Associates

[57] ABSTRACT

Health care services are made more efficient by comparing health care services from different providers independently of the clinical complexity of treating the diseases of the patients involved. This is accomplished with a computer-aided system using outpatient and inpatient claims data bases containing indicators of clinical conditions, such as age, gender, diagnoses, and procedures used, and including comparison criteria such as utilizations and indicia of quality. The diseases of the patients of the population are grouped by clinical complexity, and the extent of the systematic relationships between the clinical complexity groups and the comparison criteria are analyzed, preferably by regression analysis. With the extent of the systematic relationships to clinical complexity being known, the health care services of different providers are compared for utilization of procedures and indicia of quality, independently of the differing clinical complexity of the patients receiving the services. The health care services rendered are then modified to improve their efficiency, based on the information revealed in the comparisons.

5 Claims, 1 Drawing Sheet

OTHER PUBLICATIONS

Christensen; "'Staging' Software Measures Severity of Patients's Illness; Software Designed to Cut Through DRG Categories May Better Gauge Patients' Resource Consumption"; *Hospitals, Journal of American Hospital Association;* v58; May 1, 1984; p45(3); Dialog: File 148, Acc# 02033036.

Wieners; "Quality Measurement & Severity Systems: An Overview"; *Computers in Healthcare;* v9 n10; Oct. 1988; p27(4); Dialog: File 275, Acc# 01254734.

Berwick; "Toward Applied Technology for Quality Measurement in Health Care"; *Medical Decision Making;* v8 n4; Oct.–Dec. 1988; p.253–258.

Stern et al.; "A Comparison of Length of Stay and Costs for Health Maintenance Organization and Fee–for–Service Patients"; *Arch. Intern. Med.;* v149 n5; May 1989; p1185–1188.

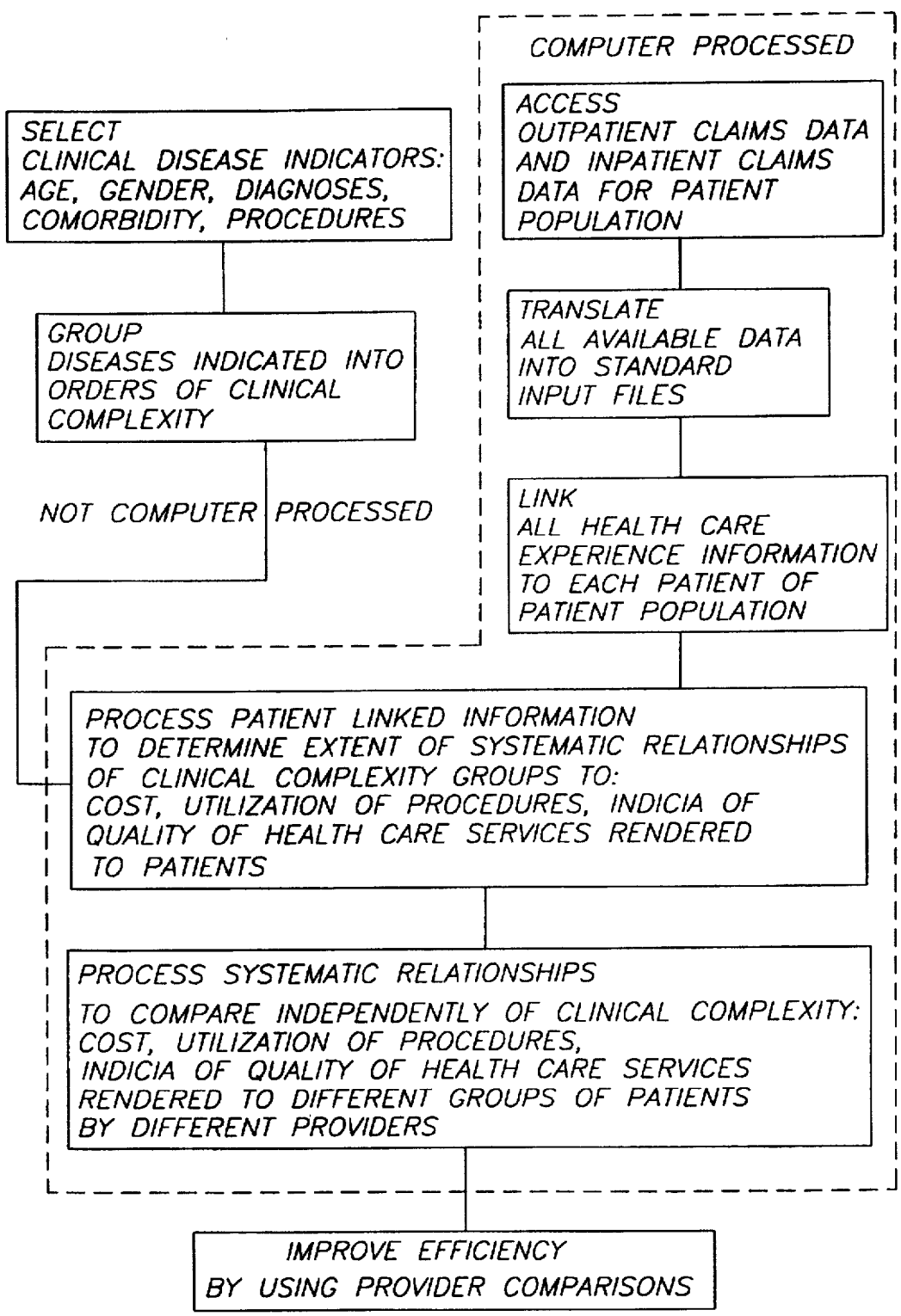

5,724,379

METHOD OF MODIFYING COMPARABLE HEALTH CARE SERVICES

RELATED APPLICATIONS

This application is a Continuation of parent application Ser. No. 08/038,351, filed 29 Mar. 1993, entitled METHOD OF MODIFYING COMPARABLE HEALTH CARE SERVICES, and abandoned upon the filing of this Continuation application, which parent application is a Continuation of abandoned grandparent application Ser. No. 07/517,257, filed 1 May 1990, entitled HEALTH CARE SERVICES COMPARISON PROCESSING. The parent and grandparent applications are hereby incorporated by reference.

BACKGROUND

Direct comparisons of quality or utilization of procedures between different providers of health care services has generally been unattainable. There has been no way of realistically determining the true needs for the services rendered, because there has been no way of knowing the comparative health of the different patients to whom the services are rendered. For example, if the services of one physician to one group of patients involve more or different utilizations than the average of similar services to similar patients by a larger group of similar physicians, the doctor rendering the more complex services can argue that the recipient patients have more complex health problems that are more difficult to treat. There has been no reliable way to determine whether such an assertion is valid; and for lack of a truly equivalent comparison basis, there has been no reliable way for group procurers of health care services to distinguish between efficient and inefficient providers of health care services so as to modify or improve the efficiency of the services.

Diagnostic related groups (DRGs) have been instituted for Medicare services as a method of making averaged payments (rather than fee-for-service payments) to different providers of health care services. DRGs have not successfully met the need for valid inter-provider comparisons, however, because they apply only to inpatient data, apply only to hospital payments, and involve many clinically unrelated diagnosis groupings. There has been much controversy with DRGs and with the comparisons derived from them.

Other comparison attempts have involved reviewing patient charts from hospital admissions to extract additional information about the health care needs and services involved, but this has been very laborious and expensive. It is not a practical solution to the need for consistently and inexpensively comparing the vast quantities of health care services being continually rendered.

SUMMARY OF THE INVENTION

We have discovered that health care services can be made more efficient by using a better way of comparing health care services from different providers. Our comparison of provider services is made independent of the clinical complexity of treating the diseases of the patients involved so that the comparisons are truly equivalent. Our method also accomplishes this with a computer-aided system using available health claims data so that the comparisons can be done inexpensively. Our method uses all the available health care experience from both inpatient claims data and outpatient claims data so as to deal with everything relevant to the health of the patients in a population. All the available health care experience information is then translated into standard input files and associated with each specific patient to reveal as much as possible about the state of each patient's health, including the diseases experienced by each patient.

Separately from the computer processing, we group the diseases experienced by the patients in the population into groups that differ from each other in the clinical complexity of treating the diseases, and we preferably rank these groups in orders of clinical complexity ranging from less clinically complex to more clinically complex. We then divide the patients of the population into the different groups of clinical complexity by assigning each patient to one of the groups based on clinical information or indicators available in the data bases for age, gender, diagnoses, and preferably comorbidity and utilization of selected procedures indicative of a patient's health status and disease history.

Then we computer process the health care experience information linked to each of the patients to determine the extent of systematic relationships of the clinical complexity groups to selected efficiency comparison criteria such as utilization of procedures, and indicia of quality of health care services rendered to patients. Once the extent of the systematic relationships of the clinical complexity groups to the comparison criteria are determined, we computer process these systematic relationships to make provider comparisons that are independent of the clinical complexity of treating the diseases of the patients involved. We can make each comparison truly equivalent, or independent of clinical complexity, by adjusting the compared criteria for the clinical complexity of the particular patients receiving the services being compared. Also, by using the systematic relationships of the compared criteria to the clinical complexity groups, we can compare utilization of procedures, and indicia of quality of health care services rendered to different groups of patients by different providers, independently of the clinical complexity of treating the diseases of the provider's patients.

This then affords a sound comparative basis for modifying the health care services rendered to the patient population to make those services more efficient. Comparisons made this way afford significant additional information to group procurers of health care services who can use this information to select providers, select services from providers, inform providers of efficiency comparisons, and otherwise ensure that the health care services being rendered to the patient population are made more efficient.

As the efficiency of health care services improves, based on the efficiency comparison information, this tends to alter the utilization of procedures and indicia of quality of the services being rendered. This can warrant a new analysis of the extent of the systematic relationships of the comparison criteria to the clinical complexity groups and can enable new efficiency comparisons, for continually improving the efficiency of health care services. At the same time, we continually refine our groupings of clinical complexity of treating the diseases. The result is to make group procurers of health care services much more informed than has previously been possible, and therefore more capable of ensuring that health care modifications lead to improved efficiencies.

DRAWING

The drawing is a schematic diagram of preferred steps in our method of processing health care service information to yield meaningful comparisons according to the invention.

DETAILED DESCRIPTION

Our invention involves comparing health care services independently of the clinical complexity of treating the diseases of the patients receiving the services so that provider comparisons made equivalent by our method can be used to improve the efficiency of the health care services. Making these comparisons involves computer processing of health care experience data to provide more useful information to group procurers of health care. The source of the data to be processed is generally claims records of health care experience covered by a health care insurance plan, an employee health plan, a health maintenance organization, or some other organization that pays for health care on a group basis. The data involved is generally in the form of claims information that have been entered into a computer, in the course of paying the claims; and the data represents the health care experience and related information on a population of patients. Although the available data has different structural and organizational forms, common inputs generally exist among the available data bases, because of the conventions normally used in the payment processing of health insurance claims. The common inputs include an identifier for the patient being treated, and an identifier for the provider of the health care service, the age and gender of the patient, a standardized code indicating each diagnosis, another standardized code indicating the procedure performed, the date and location of the service, and the procedures utilized. From this data, which is common to health care insurance records, we can derive considerable information having comparative value.

The specialty of a physician rendering a service is sometimes available directly from the data bases; and when it is, we prefer using that source for identifying physician specialty. It is also possible to determine physician specialties indirectly from the available data. To do this, we identify from other sources the specialties of a few representative physicians performing large amounts of services to the patient population. We then determine from the claims data from these physicians what procedures characterize their services to patients. Other physicians performing the same procedures are then classified with the predetermined specialty for such services. This way of determining physician specialties is advantageous because it is not labor intensive and yet still appropriately groups similar practitioners (e.g., neurosurgeons are grouped with neurosurgeons rather than with pediatricians).

Our comparison process uses all the available health experience information, to take advantage of whatever can be known about the health of the patient population represented by the data bases. Many other health care information processing systems use only inpatient data, which tends to represent the health care experiences in hospitals. Using only inpatient data, or using the available data on an episode of illness basis, as many previous health care information systems do, makes meaningful comparisons between the health care services of different providers unattainable.

Our method uses outpatient claims data, as well as inpatient claims data, so that everything available about the health experiences of the patients involved is computer accessible and is considered in our process. This information is associated or linked with each patient of the population, so as to reveal as much as possible about the state of the health and disease history of the patients involved. Previously known health care service information processing systems have not considered outpatient claims data and have not linked the available data to the patients involved. Because previous systems have generally looked only at episodes of illness (admissions to a hospital), rather than to the total health care experience of the patients involved, they could examine only information about a patient during the time of a hospital admission. This left large amounts of data on health care services inaccessible to any analysis of meaningful equivalents in the efficiency of the services being rendered.

Our method also relies on available data from claims involving health care experience, without requiring laborious examination of patient charts or other information that is not immediately accessible by computer. The costly and time-consuming chart review used to augment inpatient data for analyzing illness complexity is too prohibitively cumbersome to apply to outpatient records that are relatively numerous and dispersed. In contrast, our health care information processing system can inexpensively and efficiently take advantage of outpatient data in processing health care information to make meaningfully equivalent comparisons.

To begin our process, we first group the patient diseases into groups or orders of clinical complexity, preferably using the *International Classification of Diseases* (ICD) which provides standard clinical disease codes. We can foresee that these ICD codes will be used in the data bases so that each of the patients in the population can be assigned to one of the clinical complexity groups, based on the ICD codes and other information available in the data base. This process involves the two steps shown at the upper left of the drawing, outside the broken line enclosing the computer processing steps. Dividing diseases into groups of clinical complexity involves clinical judgment, as explained below, and can be done independently of any data base. Since we prefer that a computer process be able to determine which clinical complexity group is appropriate for each patient of the population, based on the disease history revealed by the data base for each patient, it becomes valuable to consider the clinical variables or code indicators of disease that are available in the data base for the computer process to deal with. Thus, we select a set of clinical disease indicators that we deem useful in evaluating the health and disease history of the patients in the population. The clinical indicators we select involve information that is available in the data bases, and our selections for clinical indicators include age, gender, and diagnoses for all the available health care experience and disease history information for each patient. We also preferably select as clinical indicators comorbidity, meaning the existence of a significant secondary diagnosis present in a single patient having another primary diagnosis, such that the secondary diagnosis may be reasonably expected to increase the overall treatment required for the patient. Not all combinations of diagnoses represent a comorbid status, and we have selected those that are clinically reasonable. Examples include hypertension and diabetes, a previous heart attack and diseases of the heart valves, obesity and pneumonia, and many others.

Another clinical indicator we prefer is procedures that a patient has undergone that are especially revealing about the patient's health state. Examples of highly relevant procedures include use of kidney dialysis equipment, breathing assistance equipment, or chemotherapy. The procedures we select are unlikely to be used unless a patient truly requires them, so that use of the selected procedures will present a high clinical likelihood of a patient disease adding to the treatment required for virtually all diagnoses. Inclusion of selected procedures also seeks to ensure that information about significant health problems indicated by the procedures is included in a patient's history in a fail-safe manner. Many medical procedures do not necessarily indicate a clinically complex state of health for the patient who has undergone the procedure, but the procedures we preferably select, such as those mentioned above, do reveal that the patient who has undergone them has a clinically more complex health state.

Besides selecting clinical indicators that can reveal meaningful information about the health state of the patients represented by the available data bases, we group the diseases or health states represented by the indicators into orders of clinical complexity. Then the computer is able to assign or divide each of the patients in the population into one of the clinical complexity groups, in the course of processing the patient linked information, which includes the clinical disease indicators. The selection and ranking of the diseases involve some clinical experience and judgment; and in this complexity grouping process, we consider acute diseases, chronic diseases, mental health, pregnancy, comorbidity, and other factors. It is possible to group diseases into any number of different orders of clinical complexity, but we prefer about four to five orders of clinical complexity ranging from good health to a patient with highly complex health problems. The rationale for such grouping is that clinicians and health service procurers understand distinctions between orders such as NONE, MILD, MODERATE, SEVERE, so that such orders facilitate communication and analysis. We consider pregnancy as a clinical indicator in our method, and for orders of pregnancy risk, we use rankings ordered as NONE, NOT CARRIED TO TERM, MILD, MODERATE, SEVERE.

Once our clinical complexity grouping is completed, our computer processing begins as shown at the upper right of the schematic diagram of the drawing. Our process accesses both the outpatient claims data and the inpatient claims data for a patient population covered by available data bases. All this information is then translated into standard input files so that it can all be entered consistently for computer processing according to our method. Also, all the available health care experience information is linked to each patient of the patient population so as to reveal as much knowledge as the data base permits about the state of health and disease history of each of the patients in the population.

After the available health care experience information is linked to each of the patients so that it is computer accessible on a patient basis, we are ready to begin the comparison process. This involves selecting a comparison criteria by which the health care services rendered by different providers are to be compared: one of these criteria is utilization of procedures involved in the services rendered and another is indicia of quality of the services rendered. Both criteria may be used, because information is available on both and they both relate to efficiency of the health care services rendered to the patients, and because our method seeks meaningful revelation of as much information as possible. To begin the comparison process, we computer process the health care experience information from the data bases relative to the orders of clinical complexity to determine the degree or extent to which each of the efficiency comparison criteria systematically relates to the clinical complexity groups. To do this, we prefer a regression analysis, such as explained in *Principals of Econometrics* by Henri Theil, New York, Wiley, 1971.

Our method determines the extent of specific systematic relationships with the clinical complexity groups. These preferably include utilization of procedures and indicia of quality. The utilization of procedures includes such things as blood tests, other laboratory tests, X-rays, tomography, operational procedures, office visits, and others. Overall utilization of procedures can be expected to increase as clinical complexity increases. Our methodology allows us to quantify or determine the systematic extent of that increase and then to analyze the associated distribution of utilization practices among individual providers in a meaningfully equivalent fashion that is independent of the clinical complexity of treating the patients of the different providers. Our regression analysis of the available health experience data relative to our orders of clinical complexity thus enables us to determine the extent to which various procedures relate to the clinical complexity of the health of the patients in the data base population.

Quality of health care services has long been difficult to determine, but there are some indicia that are reliable indicators of quality, and we preferably use the ones we judge to be meaningful. These can include outcomes such as mortality or complications following procedures. Some complications or poor outcomes may be expected to increase with an increase in clinical complexity. Our methodology allows us to quantify or determine the systematic extent of that increase. We can then proceed to compare the results of medical practice among individual providers in a meaningfully equivalent fashion. This is possible because regression analysis in our computer processing method can determine the extent to which such indicia of quality of health care services relate to the clinical complexity of the patients involved; and once this is determined, comparisons can be made independently of the clinical complexity of treating the diseases of the patients.

Once we determine the extent of the systematic relationships of the clinical complexity groupings to the comparison criteria of the health care services rendered, such as utilization of procedures and indicia of quality, we can then compare health care services rendered to different groups of the patient population by different providers; and we can make these comparisons independent of the differences in clinical complexity of the patients involved. These comparisons can include the health care services of one physician, such as an internist, compared with the health care services rendered to the patient population by all the internists involved; the health care services of one health maintenance organization compared with the health care services rendered to the whole patient population; and other comparisons. Such comparisons can include comparing a single internist's actual services to his portion of the patients for a given time period with the average services of the "average" internist who deals with the same age, gender, and case mix complexity of patients.

Our determination of the extent of the systematic relationships of clinical complexity orders to procedure utilizations and indicia of quality allows us to make meaningfully equivalent comparisons that are adjusted to be independent of the varying clinical complexity of the patients receiving the services. Previously, the more extensive health care rendered to more clinically complex patients of one physician made relatively invalid comparisons with the less clinically complex average of the patients of all otherwise similar physicians. The same would also be true of other providers of health care services such as HMO's, hospitals, Allied Health Professionals, etc. Adjusting for the clinical complexity of the patients being served eliminates clinical complexity as a variable so that comparisons between similar groups of providers having varying sizes and complexities of patient groups can be made independently of the different clinical complexities of the patients involved.

The meaningfully equivalent comparisons that our process produces, using patient-related data and clinical complexity groupings for the patients involved, can supply useful information on the efficiency of different health care services. This is especially valuable for organizations that procure health care services on a group basis and wish to make those services more efficient. Once the comparative efficiencies are known, the health care procurers can choose the more efficient providers, and inefficient providers, when confronted with the comparative evidence, can take steps to become more efficient. These and other measures using the efficiency comparisons can modify the services being rendered to the patient population and ensure that changes in these services lead to improved efficiency.

The changes that are expected in efficiencies of health care services procured in the light of information developed by our method may gradually alter the systematic relationships between the services and the clinical complexity groupings. This can warrant a reanalysis of the extent of those systematic relationships to adjust the relationships to reflect altered experience with the efficiency of the health care services being rendered. A new regression analysis refining the systematic relationships of the services to the clinical complexity orders may yield new information about comparative efficiencies of different providers. This in turn can further improve efficiency until all providers of health care services are working at comparable efficiencies.

Experience with the application of our method of modifying health care services is also expected to produce refinements in the ranking of clinical disease indicators into orders of clinical complexity. The ranking of the clinical complexity indicators is expected to be an ongoing process, not only to refine the practice of our invention, but to take into account new diseases, procedures, diagnoses, and indicia of quality.

We claim:

1. A method of modifying health care services rendered to a population of patients by a plurality of providers of health care services, said method comprising:
   a. dividing human diseases evident from predetermined diagnoses and procedures into at least four groups, namely, acute diseases, chronic diseases, mental health, and pregnancy and further dividing the groups into orders of clinical complexity ranging from less to more clinically complex;
   b. linking each patient of the population to the patient's respective records in a data base of health care experience information containing records of both inpatient and outpatient services including diagnoses and procedures for individual patient's multiple episodes of illness;
   c. assigning each patient a clinical complexity rating by comparing the various diagnoses and procedures linked to each patient with the ordered groups of clinical complexity into which such diagnoses and procedures were previously grouped;
   d. computer processing the data base of health care experience information to determine the extent to which the ordered groups of clinical complexity systematically relate to indicia of quality and utilization of the services rendered to the patients so that the indicia of quality and utilization can be compared independently of the ordered groups' clinical complexity;
   e. computer processing comparisons of health care services rendered by different providers to different groups of patients in the population by using the systematic relationship between the groups of clinical complexity and the indicia of quality and utilization of health care services to reveal comparative clinical efficiencies of the different providers;
   f. using the comparative provider clinical efficiencies to increase the number of the comparably more efficient health care services for patients in the population and to decrease the number of comparably less efficient health care services for patients in the population, thereby increasing the clinical efficiency of the overall rendering of health care services to the population; and
   g. completing the modification of health care services using the comparative provider clinical efficiencies so that the data base of health care experience information is modified to reflect a different systematic relationship between the groups of clinical complexity and the indicia of quality and utilization of health care services indicative of increased overall clinical efficiency of the health care services rendered to the population.

2. The method of claim 1 wherein said step of dividing human diseases evident from predetermined diagnoses and procedures includes dividing the human diseases into a fifth group, namely, comorbidity.

3. The method of claim 1 including the further steps of computer reprocessing the modified data base by steps b and c to redetermine the systematic relationships between the groups of clinical complexity and the indicia of quality and utilization of health care services, and then using the redetermined systematic relationships to computer reprocess comparisons of different providers by step e, and using the recompared clinical efficiencies of the providers to remodify the overall clinical efficiency of the health care services rendered to the population by step f.

4. A method of modifying health care services rendered to a population of patients by a plurality of providers of health care services, said method comprising:
   a. dividing human diseases evident from predetermined diagnoses and procedures into at least four groups, namely, acute diseases, chronic diseases, mental health, and pregnancy and further dividing the groups into orders of clinical complexity ranging from less to more clinically complex;
   b. linking each patient of the population to the patient's respective records in a data base of health care experience information containing records of both inpatient and outpatient services including diagnoses and procedures for individual patient's multiple episodes of illness;
   c. assigning each patient a clinical complexity rating by comparing the various diagnoses and procedures linked to each patient with the ordered groups of clinical complexity into which such diagnoses and procedures were previously grouped;
   d. using indicia of quality and utilization of services rendered to the patients in the population for comparing the health care services rendered by different providers to the patients in the population;
   e. computer processing the data base of health care experience information to determine the extent to which the ordered groups of clinical complexity systematically relate to indicia of quality and utilization of the services rendered to the patients so that the indicia of quality and utilization can be compared independently of the ordered groups' clinical complexity;
   f. grouping the patients with their assigned clinical complexity rating into groups receiving health care services from the different providers of the health care services to the patients in the population;
   g. computer processing the indicia of quality and utilization of the health care services of different providers rendered to different patient groups by using the determined systematic extent of the relationship between the orders of clinical complexity and the indicia of quality and utilization of services to reveal comparative differences between the providers;

h. using the comparative differences between the providers to modify the health care services rendered to patients in the population in ways that diminish comparative differences between providers; and i. completing the modification of health care services using the comparative differences between the providers so that the data base of health care experience information is modified to reflect a different systematic extent of relationship between the indicia of quality and utilization of services and the orders of clinical complexity indicative of diminished comparative differences between the providers.

5. The method of claim 4 wherein said step of dividing human diseases evident from predetermined diagnoses and procedures includes dividing the human diseases into a fifth group, namely, comorbidity.

* * * * *